US009855057B2

(12) United States Patent
Axelson, Jr. et al.

(10) Patent No.: US 9,855,057 B2
(45) Date of Patent: Jan. 2, 2018

(54) NATURAL ALIGNMENT KNEE INSTRUMENTS

(71) Applicant: Howmedica Osteonics Corp., Mahwah, NJ (US)

(72) Inventors: Stuart L. Axelson, Jr., Succasunna, NJ (US); Mohamed Soliman, Englewood, NJ (US); Michael C. Ferko, Warwick, NY (US); Robert Frederick Simes, Jr., Charlotte, NC (US); James H. Howell, Chester, PA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 218 days.

(21) Appl. No.: 14/747,411

(22) Filed: Jun. 23, 2015

(65) Prior Publication Data
US 2015/0289883 A1 Oct. 15, 2015

Related U.S. Application Data

(63) Continuation of application No. 14/525,595, filed on Oct. 28, 2014, now Pat. No. 9,113,957, which is a
(Continued)

(51) Int. Cl.
*A61B 17/15* (2006.01)
*A61F 2/46* (2006.01)
(Continued)

(52) U.S. Cl.
CPC ............ *A61B 17/157* (2013.01); *A61B 17/15* (2013.01); *A61B 17/154* (2013.01);
(Continued)

(58) Field of Classification Search
CPC .............. A61F 2017/0268; A61F 17/15; A61F 17/154; A61F 17/155; A61F 17/157;
(Continued)

(56) References Cited

U.S. PATENT DOCUMENTS

| 4,457,307 A | 7/1984 | Stillwell |
| 4,487,203 A | 12/1984 | Androphy |

(Continued)

FOREIGN PATENT DOCUMENTS

| EP | 947169 A2 | 10/1999 | |
| FR | 2679766 A1 * | 2/1993 | ........... A61B 17/154 |

(Continued)

OTHER PUBLICATIONS

Arthroplasty, Campbell's Operative Orthopaedics 9th Edition, vol. One, pp. 1-1076 (1998).
(Continued)

*Primary Examiner* — Larry E Waggle, Jr.
(74) *Attorney, Agent, or Firm* — Lerner, David, Littenberg, Krumholz & Mentlik, LLP

(57) ABSTRACT

A method for aligning an orthopedic implant in a joint replacement includes determining the bone and cartilage deficiency from an undegenerated state caused by wear of a joint. Then a resection of a bone in the joint is made based on the deficiency of bone and cartilage from the undegenerated state and the size of a joint implant so as to locate the joint surface of the implant in the undegenerated cartilage location. The condylar wear from the undegenerated states may be assessed at a distal and posterior location on each of a medial and a lateral femoral condyle. A distal cut is made on the femur at a location adjusting for the condylar wear from the undegenerated state. The distal cut varus-valgus angle is oriented parallel to a plane across the distal femur after adjusting for wear in the distal location on the medial and lateral condyle.

18 Claims, 13 Drawing Sheets

Related U.S. Application Data continuation of application No. 13/113,414, filed on May 23, 2011, now Pat. No. 8,974,459.

(60) Provisional application No. 61/347,045, filed on May 21, 2010.

(51) Int. Cl.
*A61B 17/56* (2006.01)
*A61B 17/02* (2006.01)

(52) U.S. Cl.
CPC ............ *A61B 17/155* (2013.01); *A61B 17/56* (2013.01); *A61F 2/4684* (2013.01); *A61B 2017/0268* (2013.01); *A61B 2017/564* (2013.01); *A61B 2017/565* (2013.01)

(58) Field of Classification Search
CPC ................ A61F 17/56; A61F 2017/564; A61F 2017/565; A61F 2/4684
See application file for complete search history.

(56) References Cited

U.S. PATENT DOCUMENTS

| | | |
|---|---|---|
| 4,524,766 A | 6/1985 | Petersen |
| 4,703,751 A | 11/1987 | Pohl |
| 4,759,350 A | 7/1988 | Dunn et al. |
| 5,037,423 A | 8/1991 | Kenna |
| 5,078,719 A | 1/1992 | Schreiber |
| 5,176,684 A | 1/1993 | Ferrante et al. |
| 5,250,050 A | 10/1993 | Poggie et al. |
| 5,415,662 A | 5/1995 | Ferrante et al. |
| 5,417,694 A | 5/1995 | Marik et al. |
| 5,445,642 A | 8/1995 | McNulty et al. |
| 5,486,178 A | 1/1996 | Hodge |
| 5,540,696 A | 7/1996 | Booth, Jr. et al. |
| 5,562,675 A | 10/1996 | McNulty et al. |
| 5,569,261 A | 10/1996 | Marik et al. |
| 5,624,444 A | 4/1997 | Wixon et al. |
| 5,662,656 A | 9/1997 | White |
| 5,669,914 A | 9/1997 | Eckhoff |
| 5,676,668 A | 10/1997 | McCue et al. |
| 5,681,316 A | 10/1997 | DeOrio et al. |
| 5,682,886 A | 11/1997 | Delp et al. |
| 5,683,397 A | 11/1997 | Vendrely et al. |
| 5,688,282 A | 11/1997 | Baron et al. |
| 5,768,134 A | 6/1998 | Swaelens et al. |
| 5,776,137 A | 7/1998 | Katz |
| 5,810,831 A | 9/1998 | D'Antonio |
| 5,879,393 A | 3/1999 | Whiteside et al. |
| 5,911,723 A | 6/1999 | Ashby et al. |
| 6,013,081 A | 1/2000 | Burkinshaw et al. |
| 6,024,746 A | 2/2000 | Katz |
| 6,106,529 A | 8/2000 | Techiera |
| 6,290,704 B1 | 9/2001 | Burkinshaw et al. |
| 6,458,135 B1 | 10/2002 | Harwin et al. |
| 6,558,391 B2 | 5/2003 | Axelson, Jr. et al. |
| 6,712,856 B1 | 3/2004 | Carignan et al. |
| 6,740,092 B2 | 5/2004 | Lombardo et al. |
| 7,128,745 B2 | 10/2006 | Masini |
| 7,184,814 B2 | 2/2007 | Lang et al. |
| 7,235,080 B2 | 6/2007 | Hodorek |
| 7,239,908 B1 | 7/2007 | Alexander et al. |
| 7,261,719 B1 | 8/2007 | Twomey et al. |
| 7,309,339 B2 | 12/2007 | Cusick et al. |
| 7,371,240 B2 | 5/2008 | Pinczewski et al. |
| 7,374,563 B2 | 5/2008 | Roger et al. |
| 7,377,924 B2 | 5/2008 | Raistrick et al. |
| 7,488,324 B1 | 2/2009 | Metzger et al. |
| 7,547,327 B2 | 6/2009 | Collazo |
| 7,569,060 B2 | 8/2009 | Faoro |
| 7,618,420 B2 | 11/2009 | Collazo |
| 7,621,920 B2 | 11/2009 | Claypool et al. |
| 7,628,793 B2 | 12/2009 | Calton et al. |
| 7,641,660 B2 | 1/2010 | Lakin et al. |
| 7,641,661 B2 | 1/2010 | Steffensmeier et al. |
| 7,641,663 B2 | 1/2010 | Hodorek |
| 7,708,740 B1 | 5/2010 | Bonutti |
| 7,727,238 B2 | 6/2010 | Seo et al. |
| 7,794,467 B2 | 9/2010 | McGinley et al. |
| 7,927,336 B2 | 4/2011 | Rasmussen |
| 8,162,949 B2 | 4/2012 | Duggineni et al. |
| 8,216,244 B2 | 7/2012 | Green, II et al. |
| 8,277,455 B2 | 10/2012 | Couture et al. |
| 8,303,597 B2 | 11/2012 | Rasmussen |
| 8,317,797 B2 | 11/2012 | Rasmussen |
| 8,361,076 B2 | 1/2013 | Roose et al. |
| 8,728,086 B2 * | 5/2014 | Smith .................. A61B 17/155 606/88 |
| 2004/0097951 A1 | 5/2004 | Steffensmeier |
| 2004/0102786 A1 | 5/2004 | Grundei |
| 2005/0059980 A1 | 3/2005 | Overes |
| 2005/0234466 A1 | 10/2005 | Stallings |
| 2006/0030855 A1 | 2/2006 | Haines |
| 2006/0058882 A1 | 3/2006 | Haines |
| 2006/0122617 A1 | 6/2006 | Lavallee et al. |
| 2006/0200163 A1 | 9/2006 | Roger et al. |
| 2006/0241634 A1 | 10/2006 | Tuttle et al. |
| 2007/0219560 A1 | 9/2007 | Hodorek |
| 2007/0270871 A1 | 11/2007 | Byrd et al. |
| 2007/0293868 A1 | 12/2007 | Delfosse et al. |
| 2008/0183178 A1 | 7/2008 | Collazo |
| 2008/0195109 A1 | 8/2008 | Hunter et al. |
| 2009/0043310 A1 | 2/2009 | Rasmussen |
| 2009/0076371 A1 | 3/2009 | Lang et al. |
| 2009/0088763 A1 | 4/2009 | Aram et al. |
| 2009/0093813 A1 | 4/2009 | Elghazaly |
| 2009/0125114 A1 | 5/2009 | May et al. |
| 2009/0131941 A1 | 5/2009 | Park et al. |
| 2009/0222103 A1 | 9/2009 | Fitz et al. |
| 2009/0270868 A1 | 10/2009 | Park et al. |
| 2009/0287216 A1 | 11/2009 | Warkentine et al. |
| 2009/0287222 A1 | 11/2009 | Lee et al. |
| 2010/0010493 A1 | 1/2010 | Dower |
| 2010/0121334 A1 | 5/2010 | Couture et al. |
| 2010/0137869 A1 | 6/2010 | Borja et al. |
| 2010/0191244 A1 | 7/2010 | White et al. |
| 2010/0211077 A1 | 8/2010 | Couture et al. |
| 2010/0217338 A1 | 8/2010 | Carroll et al. |
| 2010/0241126 A1 | 9/2010 | Ghijselings |
| 2010/0268240 A1 | 10/2010 | Mc Ginley et al. |
| 2010/0305575 A1 | 12/2010 | Wilkinson et al. |
| 2010/0331847 A1 | 12/2010 | Wilkinson et al. |
| 2010/0331848 A1 | 12/2010 | Smith et al. |
| 2011/0106095 A1 | 5/2011 | Cross et al. |
| 2011/0218545 A1 | 9/2011 | Catanzarite et al. |
| 2011/0245835 A1 | 10/2011 | Dodds et al. |
| 2012/0078254 A1 | 3/2012 | Ashby et al. |
| 2012/0089146 A1 | 4/2012 | Ferko et al. |
| 2012/0143198 A1 | 6/2012 | Boyer et al. |
| 2012/0143199 A1 | 6/2012 | Young |
| 2012/0221008 A1 | 8/2012 | Carroll et al. |
| 2012/0259342 A1 | 10/2012 | Chana et al. |
| 2012/0277751 A1 | 11/2012 | Catanzarite et al. |
| 2012/0283738 A1 | 11/2012 | Green, II et al. |
| 2012/0310246 A1 | 12/2012 | Belcher et al. |
| 2012/0316563 A1 | 12/2012 | Metzger et al. |
| 2012/0316564 A1 | 12/2012 | Serbousek et al. |
| 2013/0006250 A1 | 1/2013 | Metzger et al. |
| 2013/0006251 A1 | 1/2013 | Aram et al. |
| 2013/0060253 A1 | 3/2013 | Couture et al. |
| 2013/0096563 A1 | 4/2013 | Meade et al. |
| 2013/0123788 A1 | 5/2013 | Rasmussen |
| 2013/0144293 A1 | 6/2013 | Wilkinson |

(56) References Cited

U.S. PATENT DOCUMENTS

| | | |
|---|---|---|
| 2013/0144297 A1 | 6/2013 | Wilkinson |
| 2013/0150862 A1 | 6/2013 | Aram et al. |
| 2013/0158556 A1 | 6/2013 | Jones et al. |

FOREIGN PATENT DOCUMENTS

| | | |
|---|---|---|
| WO | 2007092614 A2 | 8/2007 |
| WO | 2013057514 A1 | 4/2013 |

OTHER PUBLICATIONS

Stephen M. Howell, MD, et al., Assessment of the Radii of the Medial and Lateral Femoral Condyles in Varus and Valgus Knees with Osteoarthritis, The Journal of Bone and Joint Surgery, Incorporated, Copyright 2010.

Stephen M. Howell, MD, Kinematic vs. mechanical alignment: What is the difference?, Ortho SuperSite, printed Oct. 15, 2010.

Stephen M. Howell, MD, et al., Letters to the Editor for Howell et al., The Journal of Bone and Joint Surgery, printed Apr. 16, 2010.

Stephen M. Howell, MD, et al., In Vivo Adduction and Reverse Axial Rotation (External) of the Tibial Component Can Be Minimized, Ortho SuperSite, http://www.orthosupersite.com, Orthopedics 2009; 32:319.

Stephen M. Howell, MD, et al., Results of an Initial Experience with Custom-fit Positioning Total Knee Arthroplasty in a Series of 48 Patients, Ortho SuperSite, http://www.orthosupersite.com, Orthopedics 2008; 31:857.

Stephen M. Howell, MD, et al., Method for Quantifying Patient Expectations and Early Recovery After Total Knee Arthroplasty, Ortho SuperSite, http://www.orthosupersite.com, Orthopedics 2009; 32:884.

Smith, et al., An In Vivo Study of the Effect of Distal Femoral Resection on Passive Knee Extension, The Journal of Arthroplasty, vol. 25, No. 7, pp. 1137-1141, 2010.

Stephen M. Howell, MD, et al., Longitudinal Shapes of the Tibia and Femur are Unrelated and Variable, Clin. Orthop Relat Res, Springer, 2009.

David S. Hungerford, MD, et al., The P.C.A. Total Knee System Surgical Technique, Howmedica, Inc., Orthopaedics Division, 1980.

Kenneth A. Krackow, M.D., The Technique of Total Knee Arthroplasty, The Johns Hopkins University School of Medicine, Department of Orthopaedic Surgery, The C.V. Mosby Company, 1990.

David S. Hungerford, M.D. and Kenneth A. Krackow, M.D., Total Joint Arthroplasty of the Knee, The Johns Hopkins University School of Medicine, Department of Orthopaedic Surgery, 1984.

\* cited by examiner

NATURAL ALIGNMENT KNEE INSTRUMENTS

CROSS-REFERENCE TO RELATED APPLICATION

The present application is a continuation of U.S. patent application Ser. No. 14/525,595, filed Oct. 28, 2014, which is a continuation of Ser. No. 13/113,414, filed May 23, 2011, which claims the benefit of the filing date of U.S. Provisional Patent Application No. 61/347,045, filed May 21, 2010, the disclosures of which are hereby incorporated herein by reference.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal or ceramic femoral implant, and a damaged portion in the proximal region of the tibia may be removed and replaced with a tibial implant having an ultra-high molecular weight polyethylene (UHMWPE) bearing. In some TKA procedures, a UHMWPE bearing may also be implanted on the posterior surface of the patella, depending on the condition of the patella.

Implants that are implanted into a damaged region may provide support and structure to the damaged region, and help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be prepared (e.g., cut, drilled, milled, reamed), to provide one or more surfaces that can align with the implant and thereby accommodate the implant.

Accuracy in implant alignment is an important factor in the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to preparation (e.g., cutting, drilling, reaming, and/or milling) of a bone, it is important to correctly determine the location at which the preparation will take place and how the bone resections will be oriented. In most surgical methods, an arthroplasty jig is used to accurately position and orient bone resection instrumentation, such as a cutting, drilling, reaming, or milling instrument on bone. The arthroplasty jig may, for example, include one or more apertures and/or slots that are configured to accept and guide such a bone resection instrument.

Femoral and tibial preparation instruments for Total Knee Arthroplasty (TKA) are known in the art and conventionally reference the intermedullary (IM) canal or extramedullary (EM) features such as the long axis of the femur and tibia. As such, standard surgical techniques are designed to align the bone preparation to the mechanical axis or anatomic axis of the patient. Typical knee instruments are shown in U.S. Pat. Nos. 4,487,203, 5,037,423 and 6,558,391.

Preoperative assessment of bone loss is advantageous for prosthesis design, for example, to reduce the likelihood of prosthesis loosening and to provide a more reliable bone restoration method for preoperative implant design, thereby improving the success rate for such procedures such as total knee arthroplasty (TKA) and partial knee arthroplasty (e.g., a unicompartment knee arthroplasty) and providing a patient-specific bone restoration method to fit an individual patient's knee features.

The current available joint reconstruction and replacement surgeries, including knee, ankle, hip, shoulder or elbow arthroplasty, are mainly based on standard guidelines and methods for acceptable performance. Taking this into account, the positioning and orientation of the arthroplasty work on a joint is based on standard values for orientation relative to the biomechanical axes, such as flexion/extension, varus/valgus, and range of motion.

One of the surgical goals of joint replacement/reconstruction should be to achieve a certain alignment relative to a load axes. However, the conventional standards are based on static load analysis and therefore may not be able to provide an optimal joint functionality for adopting individual knee features of OA patients. The methods disclosed herein provide a natural approach for bone restoration, properly balancing the unconstrained joint and ligaments surrounding the joint, and resulting in a placement of a prosthetic implant that generally restores the patient's knee to a generally pre-degenerated state.

In one embodiment, the result of the bone restoration process disclosed herein is a TKA or partial knee arthroplasty procedure that generally returns the knee to its pre-degenerated state whether that pre-degenerated state is naturally varus, valgus or neutral. In other words, if the patient's knee was naturally varus, valgus or neutral prior to degenerating, the surgical procedure will result in a knee that is generally restored to that specific natural pre-degenerated alignment, as opposed to simply making the knee have an alignment that corresponds to the mechanical axis, as is the common focus and result of most, if not all, arthroplasty procedures known in the art.

While success has been reported for traditional instruments and mechanical alignment techniques, alternative alignment methods such as anatomic or "natural" alignment are being developed. The anatomic alignment method references a "natural" or pre-arthritic state of a specific patient's anatomy. These alternative methods require new instruments designed for referencing resected and un-resected aspects of the femur and tibia. Further, these new instruments will allow for preparation and final implant position in a pre-arthritic and anatomic orientation. The following disclosure describes various instrument embodiments designed to reference resected and un-resected aspects of femoral and tibial bone and to allow for alignment of bone preparation to an anatomic orientation.

BRIEF SUMMARY OF THE INVENTION

The goal of the present invention is to provide a method and instrumentation directed toward placing a total knee implant in a position which replicates the patient's pre-arthritic alignment. This philosophy is discussed in U.S. Patent Publication No. 2009/0270868, the disclosure of which is incorporated herein by reference. This reference teaches the use of patient specific cutting guides. The present invention utilizes modified conventional instruments to achieve the same result. Alternately the same instrumentation can be used in traditional methods such as mechanical axis alignment. One aspect of the invention includes providing an anatomic distal femoral resection guide alignment assembly with the ability to adjustably reference the unresected portion of the distal femur when setting the distal femoral resection guide level and varus-valgus orientation. Another aspect provides an alternate embodiment of an anatomic distal femoral resection guide alignment assembly that allows for both reference to the unresected portion of the distal femur and adjustable reference to the anterior cortex of the femoral shaft. Another aspect of the invention is the insertion of an extramedullary rod in the distal femoral cutting block to assist in orienting the flexion/extension angle of the distal femoral resection guide with respect to the anterior thigh and femur. Another aspect of the insertion is the provision of an anterior/posterior (AP) sizer with insertable variable feet which are inserted to compensate for femoral posterior wear. A posterior referencing guide can be provided with variable feet and/or shoes of varying thickness that can be placed on the feet to set the AP and internal/external rotation of the femoral implant. The feet may be rounded in the sagittal plane to better fit the tibial geometry. The AP sizer may be provided with variable thickness boots which are inserted to compensate for femoral posterior wear.

An additional aspect of the invention is the provision of a femoral referencing tibial resection alignment system that is designed to allow for reference of the prepared distal femoral bone and, through the use of femoral condyle spacing elements, to also reference the unresected tibial surface. Further, this system allows for visualization of a joint-line in a pre-arthritic or anatomic state. Specifically, the geometry is an offset of the articulating surface of the femoral component. Peg shape is such that it does not destroy the full diameter of the hole to gain fixation during instrument use but does not ruin the full hole for implant preparation. Yet an additional aspect of the invention is the provision of an adjustable slope tibial resection guide with a conical hole that allows for degrees of tibial slope adjustability with a single fixation pin placement. A tibial cutting guide assembly that references the prepared tibial bone and has referencing members that allow for correction/refinement of the tibial cut. Refinements may include tibial slope, varus alignment, valgus alignment or any combination of those mentioned. The tibial guide has markings which indicate the implant size for proper positioning of the guide.

Another aspect of the invention is a method for aligning an orthopedic implant in a joint replacement which includes determining the bone and cartilage deficiency from an undegenerated state caused by wear of a joint. A resection of a bone is made in the joint based on the deficiency of bone and cartilage from the undegenerated state and the size of a joint implant. The resection is located to place the joint surface of the implant in the undegenerated cartilage location. If the joint is a knee joint the femoral condylar wear from the undegenerated state is assessed at a distal and posterior location on each of a medial and a lateral femoral condyles. The distal cut is then made on the femur adjusting for the condylar wear from the undegenerated state. The femoral distal cut varus-valgus angle is oriented parallel to the distal femur after adjusting for wear in the distal location on the medial and lateral condyle. Thus, when implanted, the joint very closely approximates the patient's undegenerated knee, and the transverse axis in the femoral implant is naturally aligned with the transverse axis in the femur about which the tibia flexes and extends on the femur.

Another aspect of the invention is a method for aligning an orthopedic implant in a joint replacement including determining the bone and cartilage deficiency from an undegenerated state caused by wear of a joint. A resection of a bone in the joint is based on the deficiency of bone and cartilage from the undegenerated state and the size of a joint implant so as to locate the joint surface of the implant in the undegenerated cartilage location. The method includes assessing the condylar wear from the undegenerated states at a distal and posterior location on each of a medial and a lateral femoral condyle. The distal cut is made on the femur at a location adjusting for the condylar wear from the undegenerated state. The distal cut varus-valgus angle is oriented parallel to a plane across the distal femur after adjusting for wear in the distal location on the medial and lateral condyle. Another aspect of the invention is a resection guide for resecting a proximal tibia which guide references a resected distal femoral surface and includes a tibial condylar member having a body with a proximal surface for contacting a resected planar surface of a distal femur and distal surface. A plurality of modular distal spacer elements are provided which include coupling elements for attaching the spacer elements to the distal surface of the body. A tibial resection guide is coupled to the body of the trial condylar member and is movable with respect thereto in a proximal-distal direction and rotatable with respect to the body about a medial-lateral parallel to the resected planar surface of the femur. The tibial references guide may be provided with a shoe or spacer on a posterior condyle reference portion to adjust for the thickness of cartilage wear.

BRIEF DESCRIPTION OF THE DRAWINGS

FIG. 6b is a top view of the posterior referencing feet assembly of FIG. 6a;

FIG. 6C is a rear view of the posterior referencing feet assembly of FIG. 6a;

DETAILED DESCRIPTION

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
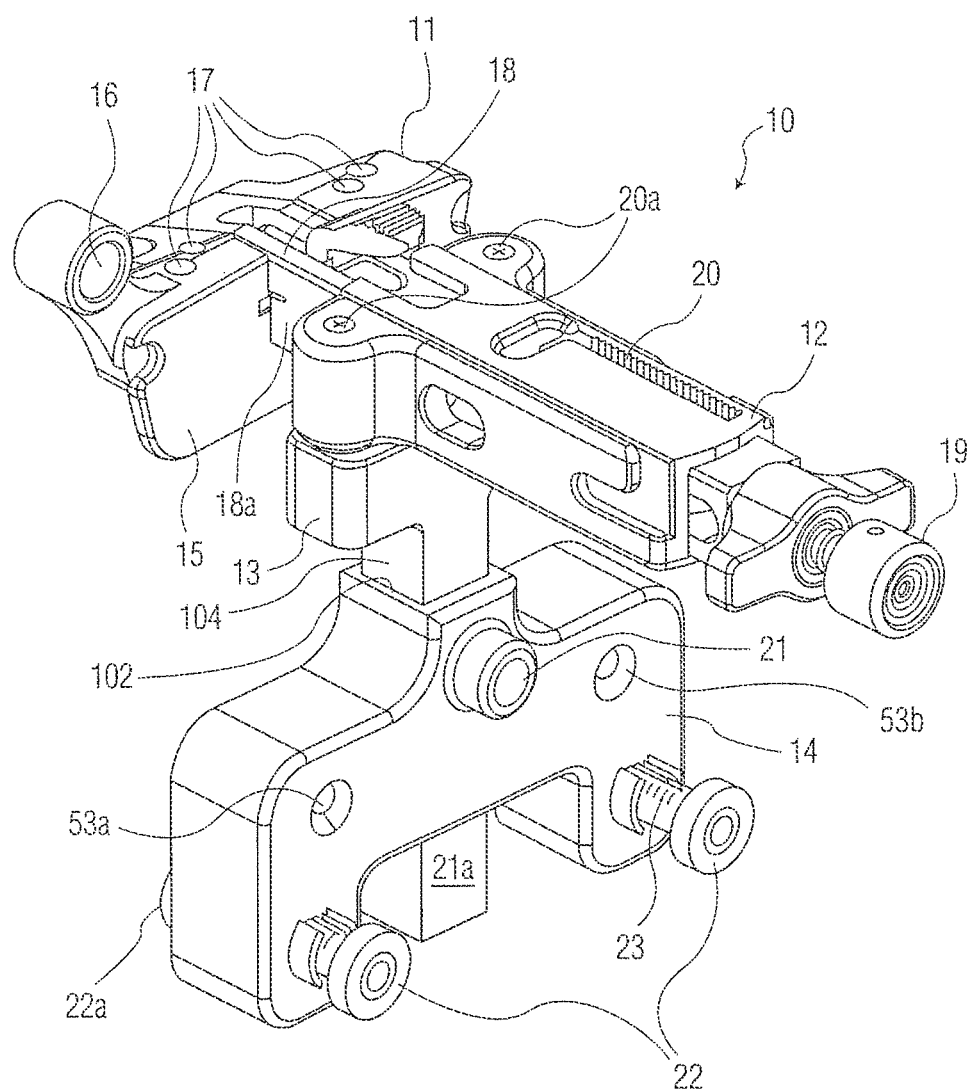
FIG. 1 is a perspective view of one embodiment of the anatomic distal femoral resection guide alignment assembly of the present invention.

Referring to the drawings, FIG. 1 illustrates a first embodiment of an anatomic distal femoral resection guide alignment assembly generally denoted as 10 which consists of a distal femoral resection guide 11 for making a distal femur planar cut, an adjustment housing 12, an AP tower 13 moveable in an AP direction and a distal femoral referencing housing 14 having adjustable pads 22a. The distal resection guide 11 includes a cutting surface 15 for guiding a saw blade, an aperture 16 for attachment to a standard navigation tracker (not shown), pin holes 17 for inserting fixation pins to an anterior surface of the femur and a connector 18 at which the adjustment housing 12 may be removably connected from resection guide 11. Connector 18 includes a shaft 18a mounted on resection guide 11 which shaft is slidably mounted in housing 12 and can be adjusted with respect thereto to locate the distal cut.

Figure 2:
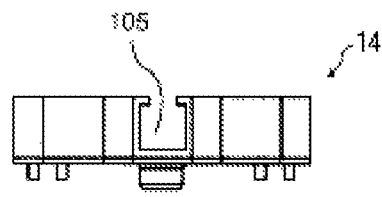
FIG. 2 is a view of the anterior facing surface of a distal femoral reference housing which forms part of the resection guide of FIG. 1.

The adjustment housing 12 may be removably or permanently connected to the AP tower 13. As shown, the housing 12 is bolted onto tower 13 by bolts or screws 20a. Further, the adjustment housing 12 may contain adjustment mechanisms such as rack 20 and pinion 19 that allow for interoperative adjustment of shaft 18a in the proximal/distal direction. AP tower 13 is preferably removably attached to distal femoral reference housing 14 via a post 104 slidably mounted in track 105 (FIG. 2). The AP tower 13 is designed to allow movement in the anterior to posterior direction and can be locked in place with a locking mechanism or locking screw 21.

The distal femoral referencing housing 14 contains two adjustable threaded elements 22 that adjust pads 22a which contact the distal femur and may be used to reference aspects of the distal femoral surface prior to resection. The pads 22a may contain spikes or other features (not shown) for fixation to the surface of the distal femur. The pads 22a allow for varus/valgus adjustment of the system by turning elements 22 which are preferably threaded into block 14 and any adjustments may be visualized by markings 23 on elements 22.

Figure 3:
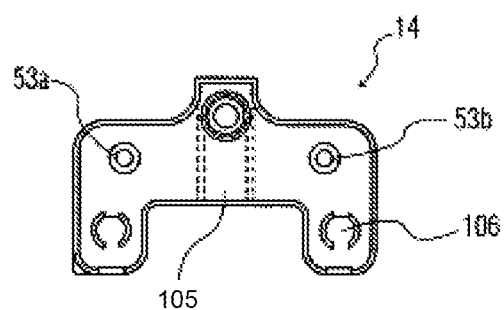
FIG. 3 is a view of the distal facing surface of the distal femoral reference housing of FIG. 2.

FIGS. 2-3 show further aspects of the distal femoral referencing housing 14. FIG. 2 shows track 105 for slidably receiving post 104 of AP tower 13. FIG. 3 shows a pair of threaded holes 106 and a pair of non-threaded bores 53a and 53b for bone pins which may be inserted into the femur. Also shown is threaded bore 21a which accommodates locking screw 21.

The method of use for the anatomic distal femoral resection guide alignment assembly 10 illustrated in FIGS. 1-3 will now be described. The proximal surface of the distal femoral referencing housing 14 contacts the unresected distal femoral surface. Here, the distal femoral surface contains cartilage which may be healthy, damaged, or non-existent depending on the progression of degeneration. The cartilage may also vary from the left and right condyles. The surgeon uses the adjustable pads 22a to compensate for any distal femoral cartilage wear which may range from 1-3 mm, for example. The surgeon may determine this by measuring a healthy condyle on the same or opposite knee. Once the surgeon has used the adjustable pads 22a to compensate for the cartilage degeneration on the distal femoral surface, the appropriate level of distal femoral resection can be adjustably set followed by pinning the distal resection guide 11 to the anterior aspect of the femoral bone via holes 17. The connector 18 is then uncoupled so a saw may be used to resect the distal femur.

Figure 4:
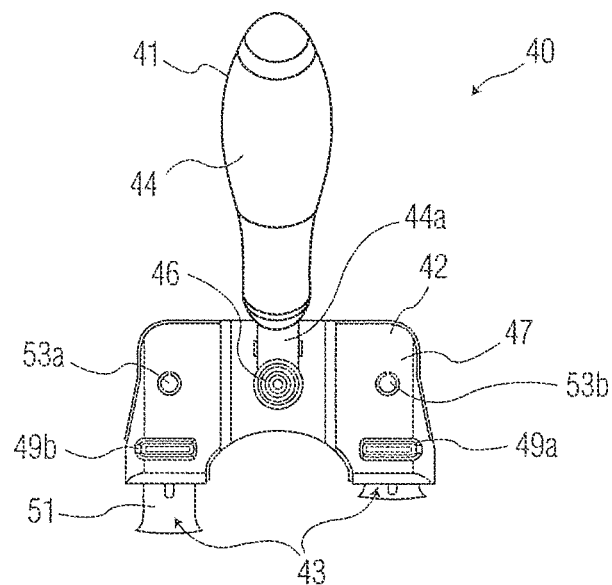
FIG. 4 is a view of the distal facing end of an AP/internal-external positioner assembly.
Figure 5:
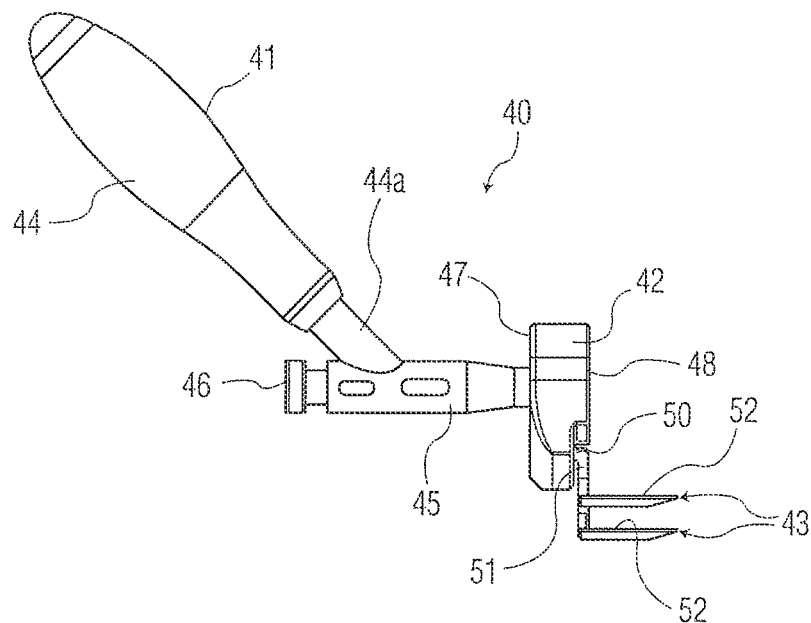
FIG. 5 is a view of the medial facing side of the AP internal-external positioner assembly of FIG. 4.
Figure 6A:
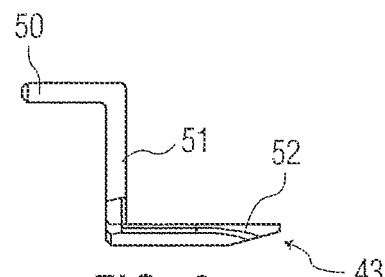
FIG. 6a is a side view of a posterior referencing foot of the assembly of FIG. 5.
Figure 6B:
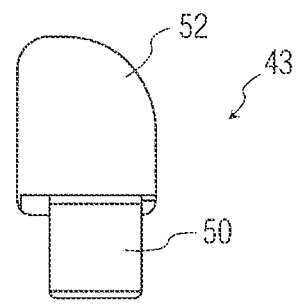
Figure 6C:
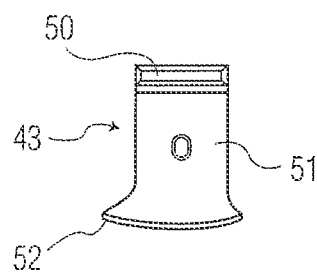
Figure 7:
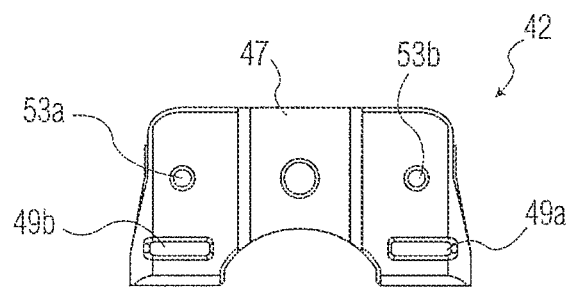
FIG. 7 is a view of the distal facing surface of the AP/IE positioner block of FIG. 4.

FIGS. 4-5 illustrate an AP positioner assembly 40 which includes a handle 41, positioner body 42 and a pair of posterior referencing feet 43. Handle 41 consists of a grip portion 44 with a neck 44a connected to a body portion 45 which can be removably attached to a distal surface 47 of the positioner body 42 by means of a locking mechanism such as a threaded knob 46. The positioner body 42 has, with respect to the femur, a flat distally facing surface 47 and a proximally facing surface 48, attachment slots 49a and 49b which extend from surface 47 to 48 and removably attachable posterior referencing feet 43. Referencing feet 43 have flanges 50 which extend through and slidably engage slots 49a and 49b. In this embodiment, proximally facing surface 48 will contact the resected planar distal surface of the femur and the posterior referencing feet 43 reference the posterior aspect of the femoral condyles prior to their resection. The posterior referencing feet 43 are removably connected to the positioner body 42 thru the attachment slots 49a and 49b and may include a locking mechanism such as a ball detent to hold them in slots 49a and 49b. Further, the posterior referencing feet 43 each have an attachment flange 50 inserted into the attachment slots 49a and 49b. Flange 50 is connected to a known length connection leg 51 and a posterior referencing arm 52. The connection leg 51 may come in multiple lengths to allow for interoperative adjustments and therefore allow for adjustments in the AP and internal-external positioning of the positioner assembly. Once the desired orientation of the positioner assembly is obtained, the positioner body may be used to align the femoral four in one resection guide. This is done by drilling through the apertures 53a and 53b. FIGS. 6a-6c illustrate a side view, a top view and a rear which of the posterior referencing feet 43. Both the medial and lateral referencing feet may be identical. FIG. 7 further illustrates the positioner body 42.

The method of use for the positioner assembly 40 illustrated in FIGS. 4-7 will now be described. The proximally facing surface 48 of positioner body 42 is placed on the resected distal end of the distal femoral bone. At this point the surgeon will insert posterior referencing feet 43 into attachment slots 49a and 49b. The posterior referencing member 52 will contact the unresected posterior cartilage on the right and left condyles of the distal femur and different thickness referencing members 52 of predetermined thicknesses (preferably in 1 mm increments) allow for the surgeon to set alignment (anterior, posterior, and internal/external rotational i.e. axial alignment) of the femoral four in one resection guide which thus aligns the final femoral implant by considering any cartilage wear on the posterior condyles. Given the modularity of the posterior referencing feet 43 and the provision of different length legs 51 allows the surgeon to make alignment modifications to align the instrument to a pre-arthritic orientation state. Shims can also be placed between the anterior surface of the feet 43 and the posterior condyles. Once proper alignment is determined, the surgeon will drill into the bone through apertures 53a and 53b. Sizing of the femoral component using this instrument would be determined by typical implant size specific four-in-one cutting blocks which relate to the available femoral components (not shown, but available in standard knee instrument kits) that interface with the holes in the bone. These holes in the bone which were drilled through bores 53a and 53b would be used to mount standard four in one cutting guides for making two anterior and two posterior chamfer cuts.

Figure 8:
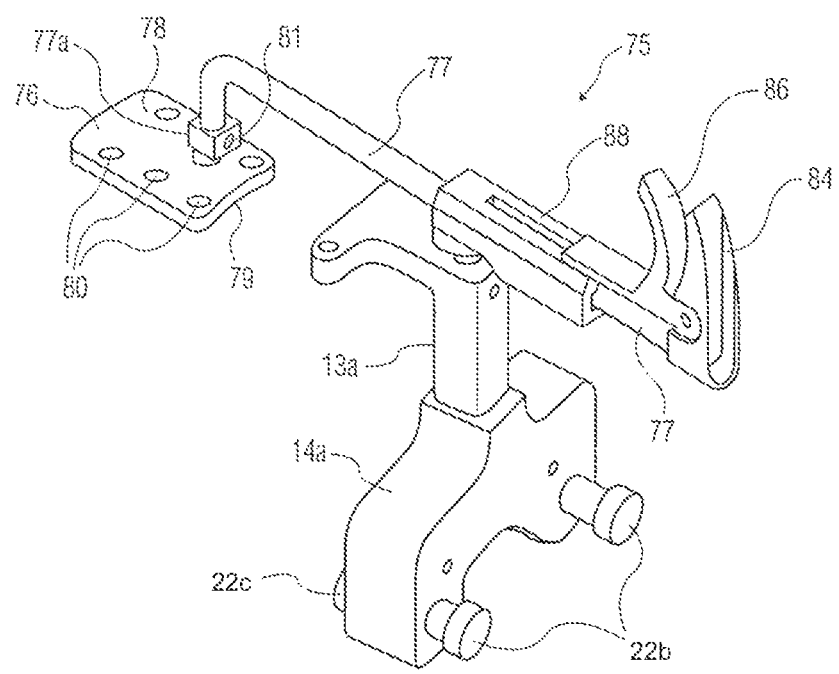
FIG. 8 is a perspective view of an alternate embodiment of the anatomic distal femoral resection guide alignment assembly.

FIG. 8 illustrates an alternate embodiment of an anatomic distal femoral resection guide alignment assembly 75. This assembly includes an anterior cortex referencing pad 76, a stylus like extension rod member 77, an AP tower 13a, a distal femoral referencing housing 14a and adjustable pads 22c adjusted by screws 22b. An important aspect of this embodiment is the anterior cortex referencing pad 76 which has an anterior facing surface 78, a posterior surface 79 which contacts the anterior cortex of the femoral bone and fixation apertures 80 to receive fixation pins (not shown). Extension rod member 77 may be adjusted in the proximal-distal direction by the actuation of handle 84. Lock 86 is used to lock the member 77 as specific points 88 on a holder 90. Pad 76 is preferably connected to extension member 77 by a hinge joint 77a which forms part of attachment mechanism 81. Hinge 77a allows for rotation of assembly 75 about a medial lateral extending axis. Further, there is an attachment mechanism 81 which allows for a pivotal connection to the stylus like extension member 77. Similar to embodiments described above, this embodiment of the distal femoral resection guide alignment assembly 75 allows for movement of the adjustment pads 22c in a proximal-distal direction with respect to the femur.

The method of use for the alternate embodiment of the anatomic distal femoral resection guide alignment assembly 75 illustrated in FIG. 8 is similar to the methods described for the instrument in FIGS. 1-3. The exception if the addition of the anterior cortex referencing pad 76 which allows for positioning of the component at different flexion angles, such as 3-5 degrees. A distal resection cutting guide is not shown in this figure, but it can be envisioned that a distal resection cutting guide similar to 11 having an anteriorly-posteriorly extending planar cutting surface can be removably connected to referencing housing 14a. Once the appropriate alignment is determined, the distal resection guide would be pinned to the anterior aspect of the bone and a distal bone resection would be made.

Figure 9:
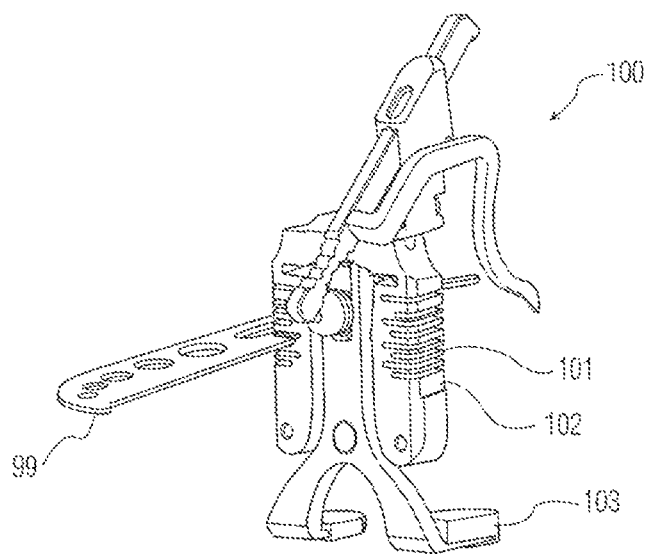
FIG. 9 is a perspective view of one embodiment of an AP sizer assembly.
Figure 10:
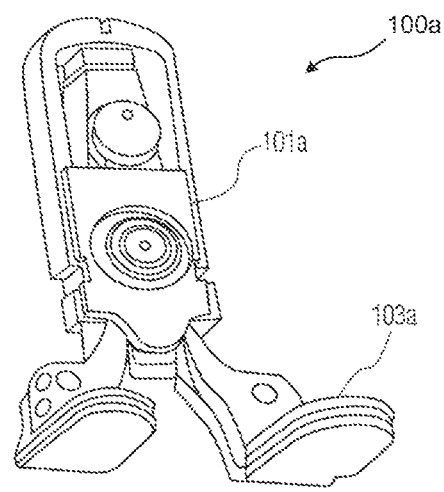
FIG. 10 is a perspective view of an alternate embodiment of an AP sizer assembly.
Figure 11:
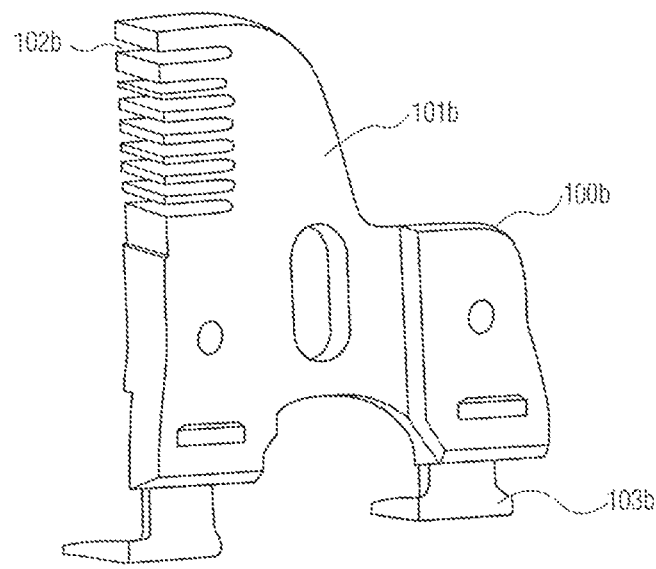
FIG. 11 is a perspective view of yet another embodiment of an AP sizer assembly.

FIGS. 9-11 illustrate various embodiments of an AP sizer assembly (100, 100a, 100b). Each assembly may consist of an AP sizer body (101, 101a, 101b) having a plurality of slots corresponding in size to available femoral components, calibrated sizing slots (102, 102b) and removably attachable posterior referencing members (103, 103a, 103b).

The method of use for different AP sizer assemblies (100, 100a, 100b), illustrated in FIGS. 9-11. Here various removably attachable posterior referencing spacers (103, 103a, 103b) may be used to compensate for any posterior cartilage wear (preferably in 1 mm increments) and an implant size for a femoral component may be determined by using a sizing stylus or sizing slots with an angle wing 99 for instance. Angle wing or blade runner plate 99 allows the surgeon to estimate the femoral implant size.

Figure 12:
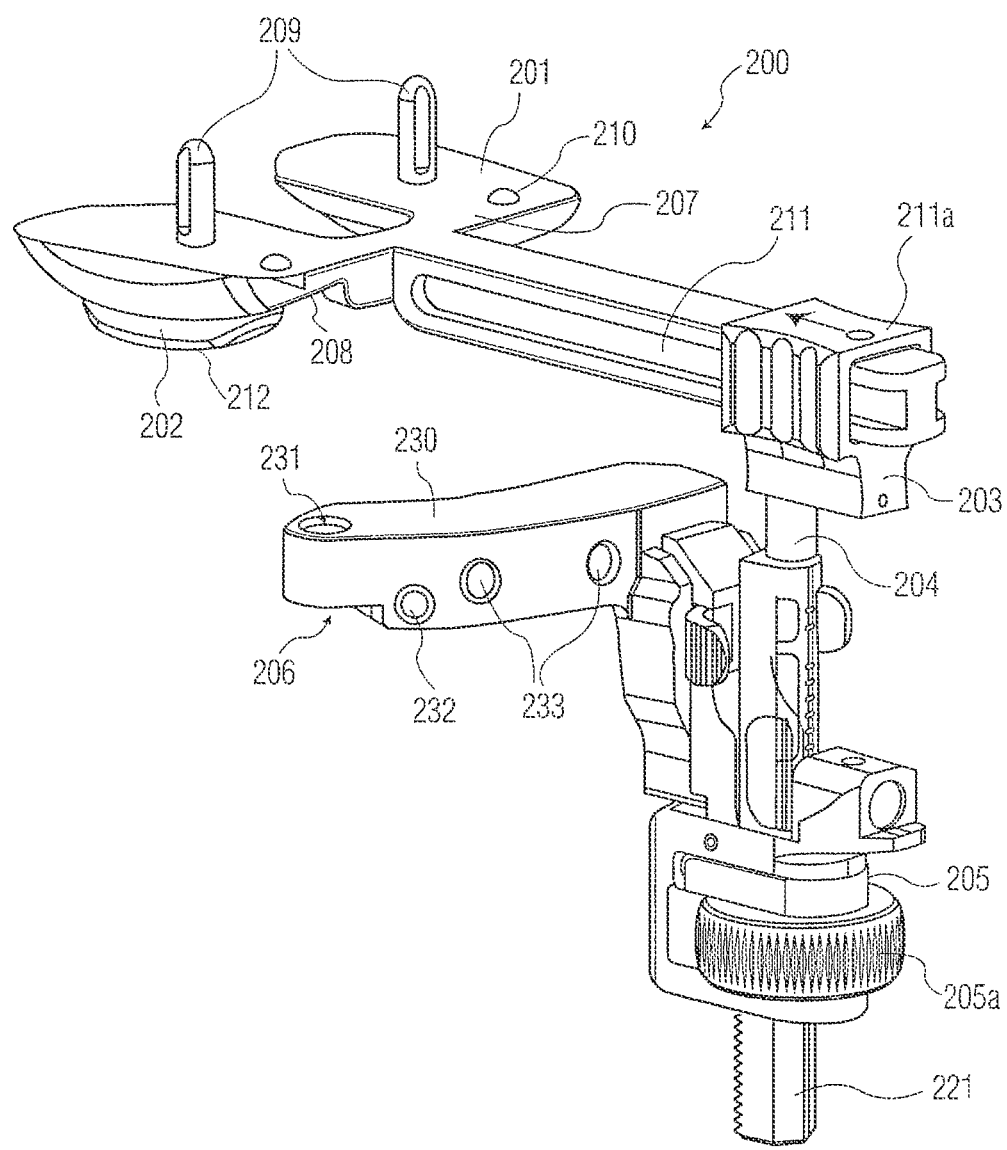
FIG. 12 is a perspective view of a femoral referencing tibial resection assembly.
Figure 13:
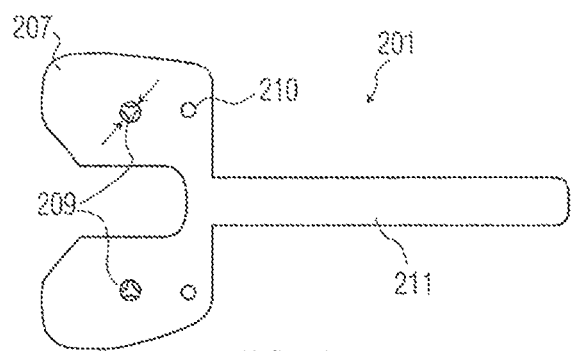
FIG. 13 is view of the proximal facing surface of a femoral referencing template.
Figure 14:
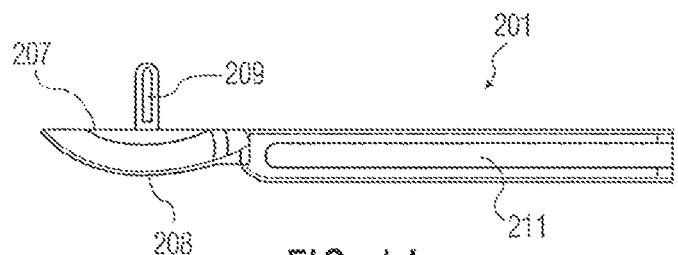
FIG. 14 is a view of the medial facing surface of the femoral referencing template of FIG. 13.
Figure 19:
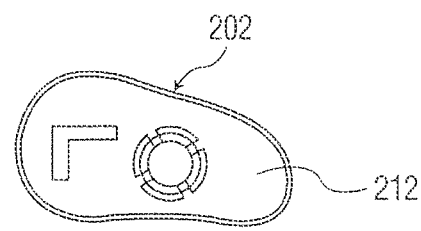
FIG. 19 is a view of the distal facing surface of a femoral spacer.
Figure 20:
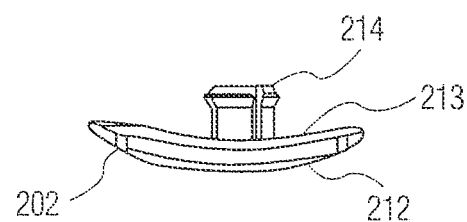
FIG. 20 is a view of the medial facing surface of the femoral spacer of FIG. 19.

FIG. 12 illustrates a femoral referencing tibial resection alignment system 200. This instrument references the resected distal femur to set the proximal tibial resection. Alignment system 200 consists of the following: a trial-like femoral referencing member 201, femoral spacer elements 202, resection guide tower 203, proximal rod 204 tibial adjustment housing 205 with adjustment wheel 205a and an adjustable slope tibial resection guide 206. The trial-like femoral referencing member 201, further illustrated in FIGS. 13-14, consists of a proximal facing surface 207, a distal facing surface 208, elongate peg members 209, fixation apertures 210 for receiving bone pins and an extension member 211. The proximal surface 207 contacts the distal surface of the prepared femoral bone and the elongate peg members 209 are received within previously prepared apertures in the prepared distal surface of the femur. The distal surface 208 contains an attachment mechanism for engaging femoral spacer elements 202. Femoral spacer elements 202, further illustrated in FIGS. 19-20, have a distal surface 212, a proximal surface 213 and a connection member 214. Elements 202 may have various thicknesses between the proximal surface 213 and distal surface 212. Preferably the thickness increases in 1 mm increments from 1 mm to 3 mm. Extension member 211 engages the resection guide tower 203 and allows for adjustments in the AP direction. In the illustrated embodiment extension 211 slides in a hollow guide 211a.

Figure 15:
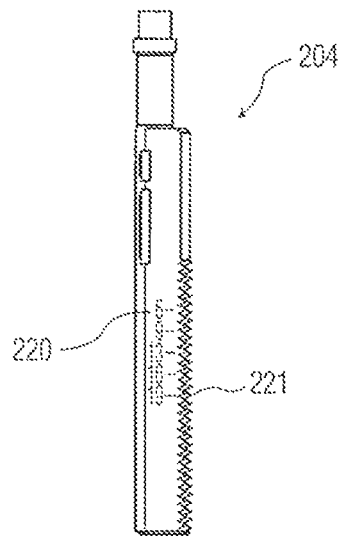
FIG. 15 is a view of the medial facing surface of the proximal rod of the tibial resection assembly of FIG. 12.

Further regarding the femoral referencing tibial resection alignment system 200, the resection guide tower 203 may be removably or permanently connected to the proximal rod 204. The rod 204, further illustrated in FIG. 15, may consist of markings 220 and thread-like features or ratchet elements 221. The markings may be spaced at 3 mm. The tibial adjustment housing 205 engages with the rod 204 and may be available in zero (0) and three (3) degree slope embodiments. The tibial adjustment housing is further described in a Stryker owned U.S. Pat. No. 7,033,361, the disclosure of which is incorporated herein by reference. The adjustable slope tibial resection guide 206 is removably attached to the tibial adjustment housing and may consist of a proximal cutting surface 230, aperture 231 for receiving a navigation tracker, cross pin fixation aperture 232 and two conical holes 233. Conical holes 233 are further illustrated in FIGS. 16-18 and allow for tibial slope adjustments from 0-5 degrees with respect to a transverse plane in the AP direction. Here a fixation pin would be inserted thru a conical hole 233, and the tibial slope which hole 233 can be adjusted and then the adjustable tibial resection guide 206 can be fixed to the proximal tibial bone by inserting an additional fixation pin through aperture 232.

Femoral referencing tibial resection alignment system 200 allows for the adjustable slope tibial resection guide 206 to be placed by referencing both the prepared distal surface of the femoral bone and the un-resected tibial surface. Further the system 200 allows for adjustability in the AP direction and proximal distal direction.

Figure 16:
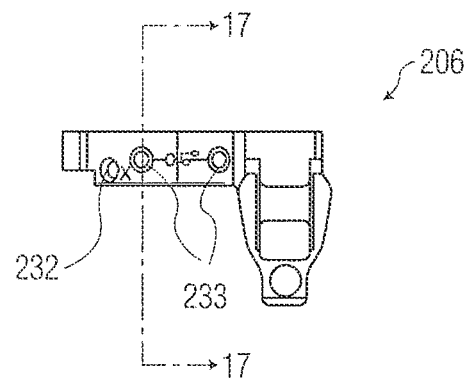
FIG. 16 is a view of the anterior facing surface of an adjustable slope tibial resection guide of the assembly of FIG. 12.
Figure 17:
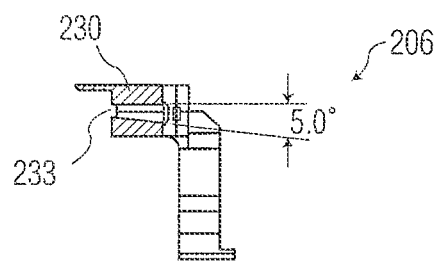
FIG. 17 is a cross sectional view of the adjustable slope tibial resection guide along lines B-B of FIG. 16.
Figure 18:
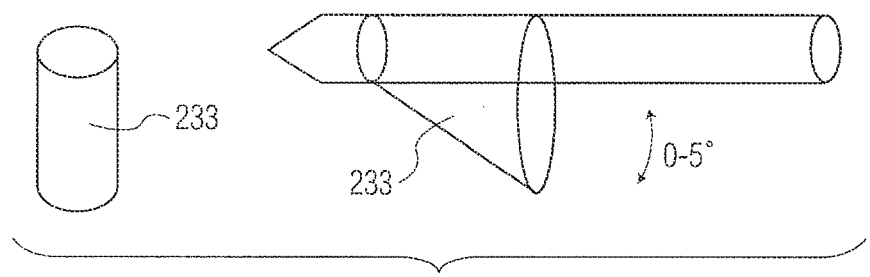
FIG. 18 is a cross sectional view of a bore through the adjustable slope tibial resection guide of FIGS. 16 and 17 with a pin extending through the bore.

The method of use for the femoral referencing tibial resection alignment system 200 illustrated in FIGS. 12-20 will now be described. The proximal surface 207 of the trial-like femoral referencing member 201 contacts the resected distal femoral bone. Elongate members 209 interface with previously made apertures in the distal femoral bone. Also, the trial-like femoral referencing member 201 may contain posterior referencing feet (not shown) to reference the posterior aspect of the distal femur. Femoral spacer elements 202 come in various thickness, such as 1, 2 or 3 mm, and are used to simulate the femoral condyles while compensating for any tibial cartilage wear, and thus allowing for restoration of the joint to the pre-arthritic state. The surgeon selects the appropriate femoral spacer elements 202 which will contact the unresected surface of the tibial cartilage surface. It should be noted that proper alignment is determined with the knee in extension. Once the surgeon has properly restored the tibial/femoral structure to a pre-arthritic state, the adjustable tibial resection guide 206 can be pinned to the anterior surface of the tibial bone. The tibial resection guide 206 has conical holes 233 which will allow the surgeon to provide a posterior slope to the tibial resection surface. For example, the conical holes 233 may allow for 0-5 degrees of posterior slope, as depicted in FIGS. 16-18.

Figure 21:
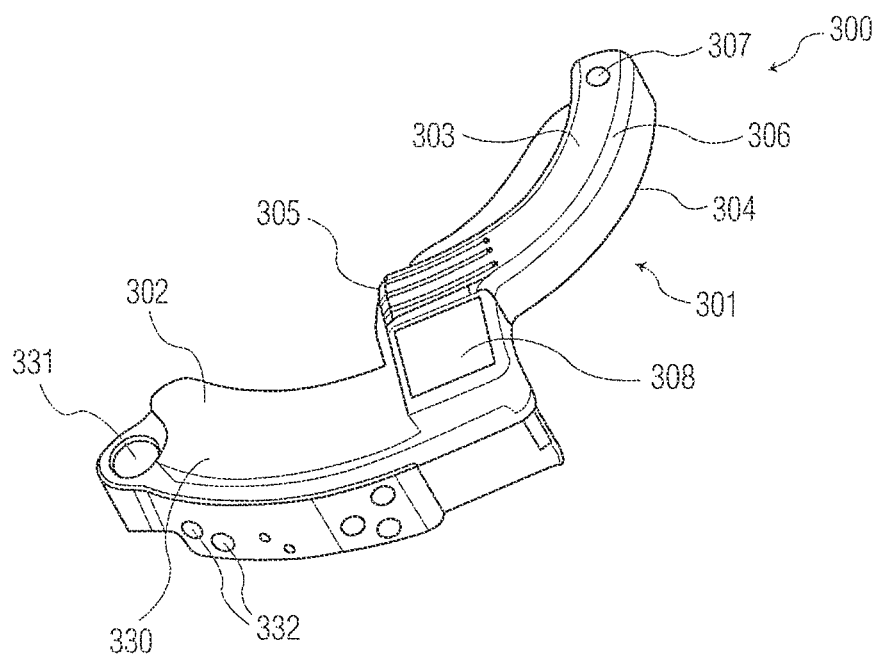
FIG. 21 is a perspective view of a tibial clean-up resection guide assembly.
Figure 22:
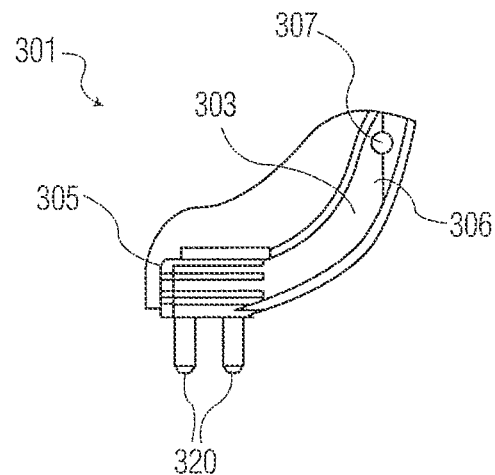
FIG. 22 is a view of the proximal facing surface of the tibial bone reference block removed from the assembly of FIG. 21.
Figure 23:
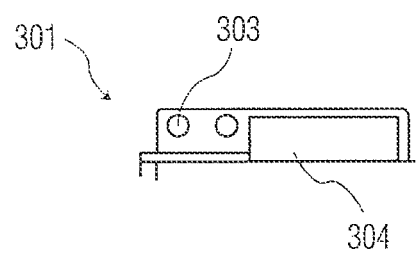
FIG. 23 is a view of the anterior facing surface of the tibial bone reference block of FIG. 22.
Figure 24:
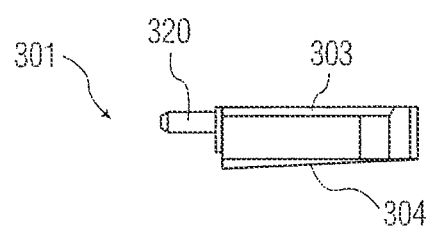
FIG. 24 is a view of the medial facing surface of the tibial bone reference block of FIG. 22.

FIG. 21 illustrates a tibial resection alignment system 300 which consists of a tibial adjustment member 301 may be removably attached to a tibial resection guide 302. The tibial adjustment member 301, further illustrated in FIGS. 22-24, preferably includes the following features: a proximal surface 303, a distal surface 304, anterior tibial cortex scribe lines 305, medial/lateral tibial scribe line 306, fixation aperture 307 and elongate connection features 320. The distance between the proximal surface 303 and distal surface 304 may be a calculated angle such as 2 degrees varus. Other such geometries can be used such to modify the tibial slope, varus alignment, valgus alignment of any combination. When in use, the distal surface 304 contacts the resected proximal surface of the tibia and elongate connection pins 320 engage connection bores in bores 308 on the tibial resection guide 302. Further, the anterior tibial cortex scribe lines 305 align with the anterior cortex of the tibial bone and the medial/lateral tibial scribe lines 306 align with the respective medial/lateral tibial cortex. The tibial resection guide 302 can be attached to the proximal tibia bone by inserting fixation pins thru apertures 332. Further, refinement cuts can be made by utilizing the proximal resection surface 330 and an appropriate surgical saw. Also, a well-known navigation tracker may be assembled to the tibial resection guide 302 at aperture 331.

The method of use for the tibial resection alignment system 300, FIGS. 21-24, will be now described. If, following a preliminary resection of the tibial surface, the surgeon considers that a "clean-up" or additional cut is desired, the surgeon can attach a tibial adjustment member 301 to a tibial resection guide 302 and make an additional cut. Here, the tibial adjustment member 301 may have various angle references to allow for additional resection in varus, valgus or other alignment.

The use of instruments described above during a surgery will now be described. First obtain a patient MRI of the knee. Determine the femoral deficiency and isolate the deficiency into distal medial, distal lateral, posterior medial, and posterior lateral areas based on the MRI. This is done through measuring normal cartilage and documenting wear in the four segments (for example 2 mm wear distal medial, zero wear distal lateral, and zero wear posterior medial and lateral). Alternately, the cartilage/bone loss can be assessed intra-operatively to determine cartilage thickness on the unaffected condyle. Other methods to determine cartilage loss are described in U.S. Patent Publication No. 2009/0270868.

Expose knee and slide a 'Z' shaped retractor along the anterior cortex of the femur proximal to the trochlea. This retractor helps determine the flexion/extension orientation of the femoral component. Drill a ⅛" pin parallel to the Z retractor into the distal most aspect of the unaffected femoral condyle (lateral for varus knee, medial for valgus knee). Assemble the distal femoral reference housing 14 of FIG. 1 by sliding it over the pin via holes 53a or 53b. Set distal resection at 8 mm by adjusting rack and pinion 19 and 20. The goal of the distal cut is to make a resection referencing the distal femur adjusting for the wear documented from the MRI or the intra-operative measurements. Slide the distal femoral resection guide alignment assembly 10 until the proximal surface of the distal femoral referencing housing 14 is in contact with the unaffected condyle. Adjust the varus/valgus setting until the proximal surface of the distal femoral referencing housing 14 is positioned parallel with the distal femur after adjusting for the wear. (For example, if there is 2 mm distal medial wear, there should be a 2 mm gap between the proximal surface of the distal femoral referencing housing 14 and the femur on the diseased side and a 0 mm gap on the lateral side. Pin the distal resection guide 11 using 2 headless pins through bores 17, remove all other instrumentation via connector 18, optionally attach a saw blade capture element, and make the distal cut. Remove the distal cut guide 11 and assemble the rotation/sizing guide of FIG. 4 and set the rotation to 0 degrees. Set femoral rotation and determine femoral implant size using the posterior referencing technique described above adjusting the posterior references 43 of the guide 40 to account for any posterior wear documented on the MRI using various leg elements. Drill through bores 53a and 53b in guide. Attach a sizing stylus as shown in FIGS. 9-11 and/or blade runner plate or wing 99 and determine the femoral size, making sure the orientation of the guide has not changed using spacer 103. After sizing is complete mount a standard 4 in 1 cutting guide (not shown) using the drilled holes. The cutting guide corresponds to one of the available femoral components. Make the anterior, posterior, posterior chamfer, and anterior chamfer cuts. To verify the femoral preparation compare the four segments that were assessed by the MRI.

Distal medial and lateral, and posterior medial and lateral segments should be approximately 6.5 mm minus wear. If there is a large variation consider adjusting femoral preparation before moving on to the tibia.

Alternatively to the sizer with the leg elements the embodiment with the shims can be used to set rotation and determine femoral implant size. The difference in the procedure would only be the use of shims to compensate for posterior wear rather than leg elements.

For tibial resection assemble the extramedullary tibiofemoral resection guide of FIG. 12 with the 0 degree slope attachment 206. In approximately 90° flexion, place guide on tibia and use standard techniques to assess the resection level of the tibia. Place the distal femoral pegs of the distal femoral trial portion into the predrilled holes in the distal femur. To accommodate for tibial compartmental wear (varus knee-medial, valgus knee-lateral) use a corresponding distal shim on the backside of the distal trial portion of the assembly. It is recommended that the remaining cartilage on the worn compartment be scraped off completely to better estimate the cartilage thickness to be accounted for (usually 2 or 3 mm). Then bring the knee slowly into extension, allowing the distal trial portion of the apparatus to sit within the proximal tibial compartments (both medial and lateral). An extra medullary alignment tower and rod can be used to assess limb alignment at this stage (flexion-extension slope and varus-valgus rotation). Proximal tibial stylus is used according to standard protocol to assess and determine the resection level. The key is to have tibia positioned against femur with this assembly in place. Pin the cutting jig 230 onto the proximal tibia, using one headless pin in the most central hole 233 available. With the patient's leg extended, attach the alignment tower and guide pin to the cutting jig and extend upwardly. Provide traction on the leg to assess the flexion/extension gaps relative to the distal femoral resection.

The tibial cutting jig is properly oriented when it indicates a tibial resection parallel to the distal femoral resection. If the cuts are not parallel, slide spacers 202 to induce a varus or valgus angle to the cutting block until the jig and distal femoral resection are parallel. Place a second pin in the cutting guide then remove the tibial alignment jig and resect the proximal tibia. If a tibial recut is required to adjust the varus valgus alignment the recut guide can be used. The appropriate recut guide is used with element 301 attached to the tibial resection guide. Component 301 is seated on the resected tibia and the scribe line is aligned to the anterior tibial cortex as is the medial/lateral scribe line 306. The resection guide is then pinned to the tibia and the cut can be made through the resection guide slot.

Figure 25:
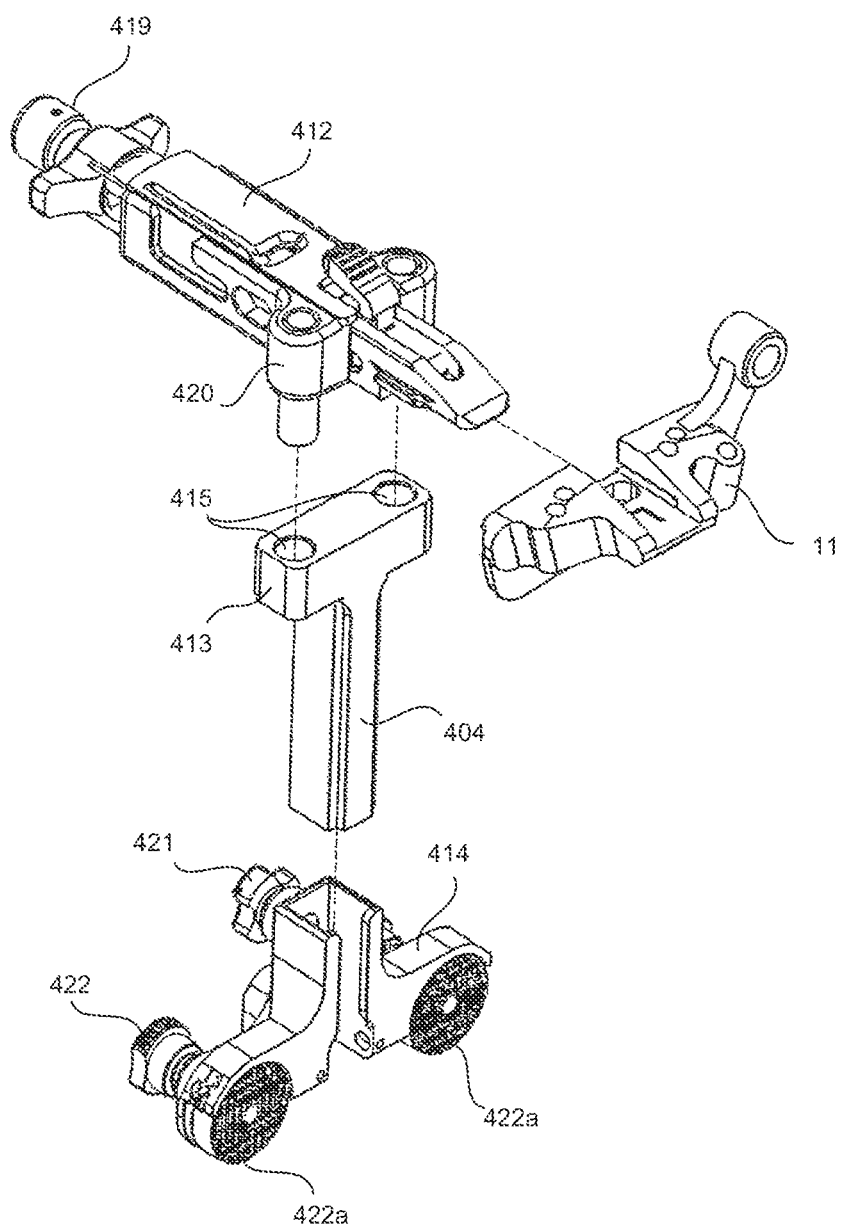
FIG. 25 is an alternate anatomic distal femoral resection guide similar to FIG. 1.

Referring to FIG. 25 there is shown an alternate distal femoral resection assembly which includes a distal femoral referencing housing 414 having adjustable pads 422a which can be adjusted by rotating screws 422. Pads 422a engage the medial and lateral distal femoral condyles respectively. The guide includes a tower 413 including a shaft 404 which is held in the distal femoral referencing housing 414 by a thumb screw 421 in the desired anterior posterior position. An adjustment housing 412 is mounted on tower 413 via a post or screw connection 420 in bores 415 of tower 413. The same distal femoral resection guide 11 as shown in FIG. 1 is used and is adjusted in the proximal distal direction by an adjustment screw 419 mounted in a housing 412.

Figure 26:
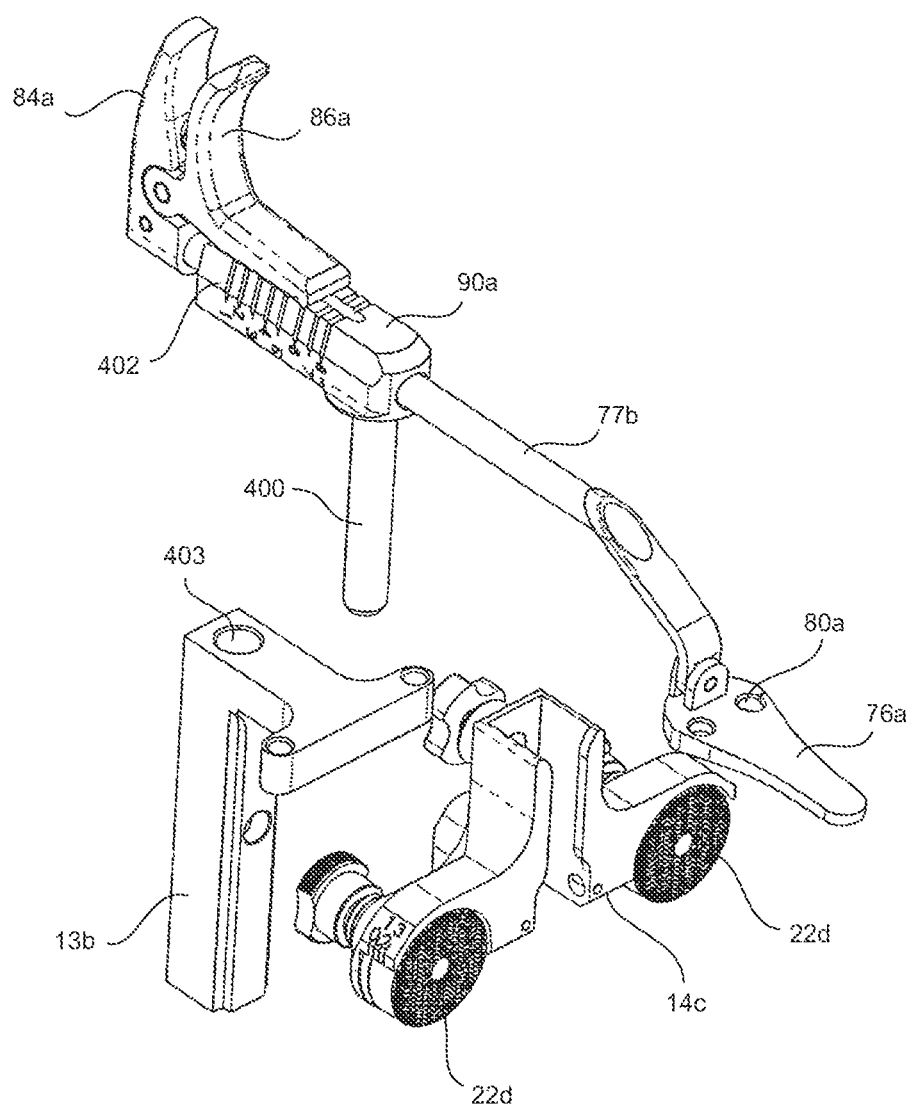
FIG. 26 is an alternate anatomic distal femoral alignment assembly similar to FIG. 8.

Referring to FIG. 26 there is shown an alternate embodiment of an anatomic distal femoral resection guide alignment assembly including an AP tower 13b, a distal femoral resection housing 14c including the adjustable pads 22d adjustable in the manner described above to set the varus/valgus orientation of the distal femoral cut. An anterior cortex referencing pad 76a is included which has a pair of pin holes 80a. Extension of rod 77b and the proximal-distal direction is accomplished via movement of handle 84a which may be locked in position by trigger lock 86a which engages grooves 402 in holder 90a. Grooves 402 may be marked in 1, 3 or 3 mm increments for reference purposes. Holder 90a is mounted on tower 13b via post 400 into a bore 403. The use of the alternate guides of FIGS. 25 and 26 is essentially the same as that described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tibial resection guide assembly, comprising:
    an elongate rod;
    a tibial resection guide adjustably mounted to the elongate rod and having a resection guide surface; and
    a femoral referencing member adjustably mounted to the elongate rod, and having a proximal facing surface for contacting a distal femur and a distal facing convexly shaped surface for contacting respective tibial condyles of a proximal tibia, the proximal facing surface including first and second peg members extending therefrom for receipt within respective openings in the distal femur.

2. The assembly of claim 1, wherein the proximal facing surface is planar.

3. The assembly of claim 1, further comprising a plurality of femoral spacer elements attachable to the distal facing surface.

4. The assembly of claim 3, wherein the plurality of femoral spacer elements each have proximal and distal surfaces defining a thickness therebetween, the thickness of each femoral spacer element being different than the thickness of the other femoral spacer elements.

5. The assembly of claim 4, wherein the thickness of the femoral spacer elements differs in 1 mm increments.

6. The assembly of claim 5, wherein the plurality of femoral spacer elements is comprised of first, second, and third femoral spacer elements, the first femoral spacer element having a thickness of 1 mm, the second femoral spacer element having a thickness of 2 mm, and the third femoral spacer element having a thickness of 3 mm.

7. The assembly of claim 3, wherein the convexly shaped surface includes attachment mechanisms for connection to one of the plurality of femoral spacer elements.

8. A tibial resection guide assembly, comprising:
    an elongate rod;
    a tibial resection guide mounted to the elongate rod between first and second ends thereof and having a resection guide surface; and
    a referencing member slidably mounted to the first end of the elongate rod, the referencing member having a proximal facing surface for contacting a distal femur and a distal facing surface having a first convex portion for contacting a proximal tibia, the proximal facing surface having a plurality of projections extending therefrom for receipt in respective openings within the distal femur.

9. The assembly of claim 8, further comprising a spacer element having proximal and distal surfaces defining a thickness therebetween.

10. The assembly of claim 9, wherein the distal surface of the referencing member includes an attachment mechanism, and the spacer element includes a connection member extending from the proximal surface thereof and configured to connect to the attachment mechanism such that the distal surface of the spacer element is offset from the distal surface of the referencing member.

11. The assembly of claim 10, wherein the attachment mechanism is located within the first convex portion.

12. The assembly of claim 9, wherein the thickness of the spacer element is one of 1 mm, 2 mm, and 3 mm.

13. The assembly of claim 9, wherein the referencing member includes a second convex portion for contacting a proximal tibia, and the first and second convex portions are separated by a space.

14. The assembly of claim 8, wherein the first end of the elongate rod includes a hollow guide configured to slidingly receive an extension of the referencing member.

15. A tibial resection guide assembly, comprising:
an elongate rod;
a tibial resection guide adjustably mounted to the elongate rod and having a resection guide surface; and
a referencing member having a body adjustably mounted to the elongate rod, the body having a proximal surface and a distal convex surface defining a thickness of the referencing member, wherein the proximal surface is planar and includes a peg member extending therefrom for receipt within an opening of a distal femur.

16. The assembly of claim 15, further comprising a spacer element connectable to the distal convex surface.

17. The assembly of claim 16, wherein the spacer element includes proximal and distal surfaces defining a thickness therebetween, and when the spacer element is connected to the distal convex surface of the referencing member, the thickness of the referencing member is increased by an amount substantially equal to the thickness of the spacer element.

18. The assembly of claim 17, wherein the thickness of the spacer element is one of 1 mm, 2 mm, and 3 mm.

* * * * *